DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 8, 1972

901 O.G. 415

T901,017
CATALYTIC HYDROGENATION

Fredrick L. Hamb and John F. Stenberg, both of Kodak Park Works, 1669 Lake Ave., Rochester, N.Y. 14650

Filed Sept. 23, 1970, Ser. No. 74,850
Int. Cl. C07c *69/54*
U.S. Cl. 260—486 R
No Drawing. 18 Pages Specification

Compounds having the structure

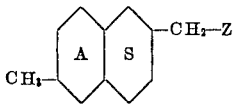

wherein

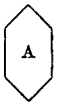

is selected from a benzene nucleus and a cyclohexane nucleus;

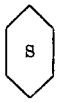

represents a cyclohexane nucleus and Z is —H or —OH, may be prepared in high yields by reducing a dialkyl 1,2,3,4-tetrahydro - 2,6 - naphthalenedicarboxylate in the presence of hydrogen and a hydrogenation catalyst such as copper chromite. The reaction may be carried out at a temperature of about 100° C. to 350° C., preferably about 140° C. to 220° C. at a pressure of about 500 to 6000 p.s.i., preferably about 1500 to 3500 p.s.i.

In another embodiment of the invention, the compounds are prepared in a two-stage reduction, the first stage comprising reducing dialkyl 2,6-naphthalenedicarboxylate in the presence of hydrogen and a nickel catalyst, such as Raney nickel to provide high selective yields of dialkyl 1,2,3,4-tetrahydro-2,6-naphthalenedicarboxylate which is subsequently reduced in a second stage reduction as aforementioned. The first reduction may be carried out at a temperature of about 25° C. to 100° C., preferably 70° C. to 85° C. at a pressure of about 100 to 5000 p.s.i., preferably 1000 to 3000 p.s.i.

Novel monomers may be prepared from the monoalcohols resulting from the reduction of the invention by condensation with acrylic acids and esters thereof such as acrylic acid, methacrylic acid, ethacrylic acid, methyl methacrylate, ethyl methacrylate and ethyl acrylate. Homopolymers or copolymers of the novel monomers may be prepared by heating the monomers by themselves or with dissimilar polymerizable ethylenically unsaturated monomers in the presence of free-radical initiating catalysts such as hydrogen peroxide, benzoyl peroxide, lauroyl peroxide, sodium persulfate, potassium persulfate and peracetic acid, for example.

The polymers which can be prepared from the novel monomer compounds of the invention in the manner just described can be used to prepare photographic film supports using known techniques.